United States Patent
Levy

(10) Patent No.: US 7,608,393 B2
(45) Date of Patent: Oct. 27, 2009

(54) METHODS OF PREDICTING A BENEFIT OF ANTIOXIDANT THERAPY FOR PREVENTION OF CARDIOVASCULAR DISEASE IN HYPERGLYCEMIC PATIENTS

(75) Inventor: Andrew P. Levy, Kiryat Shmuel (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 0 days.

(21) Appl. No.: 10/748,177

(22) Filed: Dec. 31, 2003

(65) Prior Publication Data

US 2004/0229244 A1 Nov. 18, 2004

Related U.S. Application Data

(63) Continuation-in-part of application No. 10/645,530, filed on Aug. 22, 2003, now abandoned, which is a continuation of application No. 09/815,016, filed on Mar. 23, 2001, now Pat. No. 6,613,519, which is a continuation-in-part of application No. 09/556,469, filed on Apr. 20, 2000, now Pat. No. 6,251,608.

(60) Provisional application No. 60/273,538, filed on Mar. 7, 2001, provisional application No. 60/437,439, filed on Jan. 2, 2003.

(51) Int. Cl.
C07H 21/04 (2006.01)
C12Q 1/68 (2006.01)
G01N 33/53 (2006.01)

(52) U.S. Cl. .......................... 435/6; 435/91.1; 435/7.1; 536/23.1; 536/24.3; 530/350

(58) Field of Classification Search .................. None
See application file for complete search history.

(56) References Cited

FOREIGN PATENT DOCUMENTS

| WO | WO 9001069 | 2/1990 |
| WO | WO 98/37419 | 8/1998 |
| WO | WO 01/80712 A2 | 11/2001 |
| WO | WO 2004/060135 A2 | 7/2004 |

OTHER PUBLICATIONS

Levy et al. Diabetes Care, vol. 27, No. 4, pp. 925-930, Apr. 2004.*
N England J. Med, vol. 349, pp. 60-72, 2003.*
Levy (Diabetes Care, vol. 27, No. 11, pp. 2767, Nov. 2004).*
Levy (Pharmacology & Therapeutics, vol. 112, pp. 501-512, 2006).*
Bublin, et al, Eur Heart J. 2003; 24:2099-2107.
De Bacquer, et al, Athcrosclerosis 2001; 157:161-1666.
Hong, et al, Hum Hered 1997; 47:283-7.
Hope Study Investigators NE J. Med 2000;342:154-160.
Lind, et al, Angiology 2003; 54:401-410.
Nishikawa, et al, Nature 2000; 404:787-790.
Ohgami, et al, J Diabetes Complic 2002; 16:56-59.
Stamler, et al, Diabetes Care 1993; 16: 434-444.
Steinberg D, (1997) Low density lipoprotein oxidation and its pathobiological significance.: J Biol Chem; 272-20963-6.
Williams, et al, (1992) "Dietary vitamin E and the attenuation of early lesion development in modified Watanabe rabbits. Atherosclerosis." Atherosclerosis; 94:153-159.
Brown, et al, "Simvastatin and niacin, antioxidant vitamins, or the combination for the prevention of coronary disease." NE J Med 2001; 345: 1538-92.
Gissi, Lancet 1999; 354:4477-55.
Hodis, et al, Circulation 2002; 106:1453-59.
Jiang, et al, J Biol Chem 202; 277:31850-6.
Levy, et al, J Am Coll Card 2002; 40: 1984-90.
Marchioli, et al, Lipids; 2001: 36 Suppl: S53-63.
Melamed-Frank, et al, Blood 2001; 98: 3693-98.
Steinberg, et al, Circulation 2002; 105: 2107-2111.
UK Prospective Study Group Diab Care 1998; 21: 1271-1277.
Waters, et al, JAMA 2002; 288: 2342-40.
Witztum, et al, Trends Cardio Med 2001; 11:93-102.
Barany, PCR Methods and Applic., 1:5 (1991).
Barany, Proc. Natl Acad. Sci., 88: 189 (1991).
Brown, et al, N Eng J Med 2001; 345: 1583-1592.
Fahy, et al, "Self-sustained sequence replication (3SR): an isothermal transcription- based amplification system alternative to PCR." PCR Meth. Appl., 1:25-33 (1991).
Guatelli, et al, Proc. Natl Acad. Sci., 87:1874-1878 (1990).
Mullis, PCR Methods Applic. 1:1 (1991).
The Heart Outcomes Prevention Evaluation Study Investigators N Eng J Med 2000; 342: 154-160.
Wu and Wallacc, Genomics 4: 560 (1989).
Barlow and Lehrach, Trends Genet., 3:167 (1987).
Conner, et al, Proc. Natl Acad. Sci. 80: 278-282 (1983).
Farr, et al, Proc. Natl. Acad. Sci. 85: 1629-1633 (1988).
Gogos, et al, "Detection of single base mismatches of thymine and cytosine residues by potassium permanganate and hydroxylamine in the presence of tetralkylammonium salts." Nucl. Acids Res., 18: 6807-6817 (1990).
Kwok, et al, Nucl. Acids Res., 18:999 (1990).
Lyons, et al, Science 249: 655-659 (1990).
Perlman and Butow, Science 246: 1106 (1989).
Urdea, et al, Gene 61: 253-264 (1987).
Vogelstein, et al, N Eng. J. Med. 319: 525-532 (1988).
Abrams, et al, Genomics 7: 463-475 (1990).

(Continued)

*Primary Examiner*—Jeanine A Goldberg
(74) *Attorney, Agent, or Firm*—Pearl Cohen Zedek Latzer, LLP; Mark S. Cohen

(57) ABSTRACT

A method of determining a potential of a diabetic patient to benefit from anti oxidant therapy for treatment of a vascular complication, the method comprising determining a haptoglobin phenotype of the diabetic patient and thereby determining the potential of the diabetic patient to benefit from said anti oxidant therapy, whereby a patient having a haptoglobin 2-2 phenotype benefits from anti oxidant therapy more than a patient having a haptoglobin 1-2 phenotype or a patient having a haptoglobin 1-1 phenotype.

20 Claims, No Drawings

OTHER PUBLICATIONS

Borrensen, et al, Proc. Natl Acad. Sci. USA 88: 8405 (1991).
Hayashi, Sekya and collegues PCR Meth. Appl. 1: 34-38 (1991).
Lerman and Silverstein, Meth Enzymol, 155: 482-501 (1987).
Liu and Sommer, PCR Methods Applic 4: 97 (1994).
Orita, et al, Genomics 5: 874-879 (1989).
Scholtz, et al, Hum. Mol. Genet. 2: 2155 (1993).
Sheffield, et al, Proc Natl. Acad. Sci. 86: 232-236 (1989).
Smith, et al, Genomics 3:217-223 (1988).
Wartell, et al, Nucl. Acids Res., 18: 2699-2701 (1990).
Campo, et al, Cardiovasc Drug Rev 1997; 15: 157-173.
Kita, et al, PNAS USA 1987; 84: 7725.
Mak, et al, Pharma Res. 2002; 45: 27-33.
Meng, et al, Bioorg Med Chem Ltrs 2002; 12: 2545-48.
Sagach, et al, Pharma Res 202; 45: 435-439.
Yoshida, et al, Altheroscler 2002; 162: 111-117.
Blum et al.; Journal of the American College of Cardiology vol. 49 No. 1, 2007.
Milman et al.; Vitamin E Supplementation Reduces Cardiovasuclar Events in a Subgroup of Middle-Aged Individual With Both Type 2 Diabetes Mellitus and the Haptoglobin 2-2 Genotype; Journal of the Amercia Heart Association Nov. 21, 2007.
Supplementary European Search Report Issued in EP 04 79 9315; Jun. 26, 2009.
Office Action Issued in CN 2003801180094.8; Jun. 5, 2009.

* cited by examiner

SEQUENCE LISTING

<160> NUMBER OF SEQ ID NOS: 1

<210> SEQ ID NO 1
<211> LENGTH: 21
<212> TYPE: PRT
<213> ORGANISM: human
<220> FEATURE:
<223> OTHER INFORMATION: haptoglobin peptide alpha 2 chain

<400> SEQUENCE: 1

Ala Val Gly Asp Lys Leu Pro Glu Cys Glu Ala Asp Asp Gly Gln Pro
              5                   10                  15

Pro Pro Lys Cys Ile
            20

METHODS OF PREDICTING A BENEFIT OF ANTIOXIDANT THERAPY FOR PREVENTION OF CARDIOVASCULAR DISEASE IN HYPERGLYCEMIC PATIENTS

CROSS-REFERENCE TO RELATED APPLICATIONS

This is a continuation-in-part of U.S. patent application Ser. No. 10/645,530, filed Aug. 22, 2003, abandoned, which is a continuation of U.S. patent application Ser. No. 09/815,016, filed Mar. 23, 2001, now U.S. Pat. No. 6,613,519, issued Sep. 2, 2003, which is a continuation-in-part of U.S. patent application Ser. No. 09/556,469, filed Apr. 20, 2000, now U.S. Pat. No. 6,251,608, issued Jun. 26, 2001, and which also claims the benefit of priority from U.S. Provisional Patent Application No. 60/273,538, filed Mar. 7, 2001. This Application also claims the benefit of priority from U.S. Provisional Patent Application No. 60/437,439, filed Jan. 2, 2003. The contents of all of the above listed applications are hereby incorporated in full by reference.

FIELD AND BACKGROUND OF THE INVENTION

The present invention relates to a method of determining the prospective benefits of antioxidant supplementation for prevention of cardiovascular disease in diabetic patients, based on polymorphism at the haptoglobin 2 allele.

Cardiovascular disease (CVD) is the most frequent, severe and costly complication of type 2 diabetes.[1] It is the leading cause of death among patients with type 2 diabetes regardless of diabetes duration.[2] Several population-based studies have consistently shown that the relative risk of CVD in diabetic individuals is several fold higher compared to those without diabetes.[3-7] This increased risk appears to be even more striking in women.[4,5,8] Risk factors such as hypertension, hyperlipidemia and cigarette smoking all independently increase the relative risk of the diabetic patient of developing CVD, but the effect of diabetes appears to be independent of conventional risk factors.[9]

While the incidence of CVD is higher in diabetic patients as compared to non-diabetics in all populations studied, there exist clear geographic and ethnic differences in the relative risk of CVD among diabetic patients that cannot be entirely explained by differences in conventional cardiac risk factors between these groups.[10-20] For example, analysis of the relative risk of CVD in different ethnic groups living in the United Kingdom has shown that diabetic patients of South Asian origin have a markedly increased risk[12,15], while African-Caribbean diabetic patients have a markedly decreased risk[14,16] of CVD as compared to diabetic patients of European origin.

These studies suggest that genetic differences could contribute to differences in susceptibility to CVD in the diabetic patient.

While conceiving the present invention it was hypothesized that a possibility is a functional allelic polymorphism in the haptoglobin gene.

Haptoglobin (Hp) is a hemoglobin-binding serum protein which plays a major role in the protection against heme-driven oxidative stress.[23,24] Mice lacking the Hp gene demonstrate a dramatic increase in oxidative stress and oxidative tissue damage particularly in the kidney. In man, there are two common alleles for Hp (1 and 2) manifesting as three major phenotypes 1-1,2-1 and 2-2.[21-23]

Functional differences in the hemoglobin-binding capacity of the three phenotypes have been demonstrated. Hp in patients with the Hp 1-1 phenotype is able to bind more hemoglobin on a per gram basis than Hps containing products of the haptoglobin 2 allele.[23] Haptoglobin molecules in patients with the haptoglobin 1-1 phenotype are also more efficient antioxidants, since the smaller size of haptoglobin 1-1 facilitates its entry to extravascular sites of oxidative tissue injury compared to products of the haptoglobin 2 allele. This also includes a significantly greater glomerular sieving of haptoglobin in patients with haptoglobin 1-1.[22]

The haptoglobin 2 allele appears to have arisen from the 1 allele via a partial gene duplication event approximately 20 million years ago and to have spread in the world population as a result of selective pressures related to resistance to infectious agents.[24,25] Presently the haptoglobin alleles differ dramatically in their relative frequency among different ethnic groups.[26] The gene duplication event has resulted in a dramatic change in the biophysical and biochemical properties of the haptoglobin protein encoded by each of the 2 alleles. For example, the protein product of the 1 allele appears to be a superior antioxidant compared to that produced by the 2 allele.[23] The haptoglobin phenotype of any individual, 1-1, 2-1 or 2-2, is readily determined from 10 microliters of plasma by gel electrophoresis.

It was recently demonstrated that the haptoglobin phenotype is predictive of the development of a number of microvascular complications in the diabetic patient.[27-29] Specifically, it was shown that patients who are homozygous for the haptoglobin 1 allele are at decreased risk for developing retinopathy and nephropathy. This effect, at least for nephropathy, has been observed in both type 1 and type 2 diabetic patients and the relevance strengthened by the finding of a gradient effect with respect to the number of haptoglobin 2 alleles and the development of nephropathy.[29] Furthermore, it was shown that the haptoglobin phenotype may be predictive of the development of macrovascular complications in the diabetic patient. We have shown that the development of restenosis after percutaneous coronary angioplasty is significantly decreased in diabetic patients with the 1-1 haptoglobin phenotype.[27,30] Previous retrospective and cross-sectional studies examining haptoglobin phenotype and coronary artery disease in the general population have yielded conflicting results.[31-38] The role of haptoglobin phenotype in the development of atherosclerotic coronary artery disease in the diabetic state has not been studied.

American Indians, previously thought to be resistant to developing coronary artery disease, are presently experiencing CVD in epidemic proportions.[20] This increased incidence of CVD has been attributed to the sharp increase in type 2 diabetes in this population.[1,2] The Strong Heart Study has examined the incidence, prevalence and risk factors of cardiovascular disease in American Indian populations in three geographic areas since 1988 with continued surveillance to the present.[20] The relative genetic homogeneity of this population of patients may permit identification of specific genetic factors that contribute to CVD disease in the diabetic state.

Accordingly, in U.S. Pat. No. 6,613,519, correlation was made, for the first time, for determining the relative risk of CVD in diabetic patients according to haptoglobin phenotype in a case/control sample from the Strong Heart Study.

Some prior art publications teach methods of correlating haptoglobin phenotype and disease. WO98/37419 teaches a method and kit for determining a haptoglobin phenotype and specifically relates to applications involving human haptoglobin. Teachings of this application focus on use of the haptoglobin 2-2 phenotype as an independent risk factor, specifically in relation to target organ damage in refractory essential hypertension, in relation to atherosclerosis (in the general population) and acute myocardial infarction and in relation to mortality from HIV infection. This application does not teach the use of haptoglobin phenotype as a risk factor in cardiovascular disease in DM. Because of the tendency of a haptoglobin 2-2 phenotype to make patients more prone to oxidative stress, it might be argued that use of a 2-2 phenotype as a negative predictor for cardiovascular disease in DM is indirectly implied by this patent. However, teachings of this patent do not include the idea that haptoglobin 1-1 phenotype is a positive predictor for reduced tendency towards cardiovascular disease in DM, or for the effects of antioxidant supplementation. Indeed, in a later study, the authors of PCT WO98/37419 reported opposite results, concluding that Hp 1-1 patients are at elevated risk for cardiovascular disease mortality (De Bacquer et al, Atherosclerosis 2001; 157:161-6). Deriving useful correlations between haptoglobin phenotype and disease requires careful and imaginative analysis, since many studies have reported no or confounding results (Buhlin et al Eur Heart J 2003; 24:2099-107; Lind et al Angiology 2003;54:401-10; Hong et al Hum Hered 1997;47: 283-7).

In other words, it has been proposed that oxidative stress originating from Hp 2-1 or 2-2 phenotype leads to vascular complications in the general populations. It is also known that certain vascular complications are associated with oxidative stress associated with DM. At present, however, it remains unclear, and cannot be predicted, whether Hp1-1 phenotype can affect the response to antioxidant supplementation for prevention of vascular complications in diabetic patients.

Teachings of PCT WO98/37419 include use of a haptoglobin binding partner. The binding partner according to PCT WO98/37419 may be any molecule with at least two locations by which it binds haptoglobin. The locations may be formed by a peptide, antibody, or a portion thereof, or by a lectin, a cell receptor, a molecular imprint or a bacterial antigen or a portion thereof. Teachings of this patent focus specifically on the use of the T4 antigen of *S. pyogenes*. All haptoglobins contain both alpha chains and beta chains. Beta chains are identical in all haptoglobins, while alpha chains differ between the two alleles of the haptoglobin gene. The alpha 2 chain of haptoglobin is the result of a mutation based on an unequal crossing over and includes 142 amino acids, in contrast to the 83 amino acids of the alpha 1 chain. Immunologically the alpha 1 and alpha 2 chains are similar, with the exception of a unique sequence of amino acid residues in the alpha 2 chain (Ala-Val-Gly-Asp-Lys-Leu-Pro-Glu-Cys-Glu-Ala-Asp-Asp-Gly-Gln-Pro-Pro-Pr o-Lys-Cys-Ile, SEQ ID NO:1). Any portion of this unique peptide sequence is therefore a suitable epitope for raising antibodies to differentiate between haptoglobins containing alpha 1 and alpha 2 chains as described in "Using Antibodies: A Laboratory Manual" (Ed Harlow and David Lane eds., Cold Spring Harbor Laboratory Press (1999)) which is fully incorporated herein by reference. Such antibodies might be monoclonal, polyclonal, or any portion thereof and may be enriched or purified by any one of a number of techniques known to those skilled in the art. In addition, the nucleotide sequence encoding this sequence can be readily employed to differentiate among Hp genotypes.

Antioxidants, Haptoglobin and prevention of Cardiovascular Disease (CVD) in Diabetic Patients: The overall prevalence of coronary artery disease is over 55% in adult diabetes mellitus (DM) compared to 2-4% of the general population. Mortality from CVD is more than doubled in men and quadrupled in women who have DM compared with non-diabetics (Stamler, et al. Diabetes Care 1993; 16: 434-444). An increase in oxidative stress represents an attractive unifying mechanism explaining the coordinate activation of several signal transduction pathways known to mediate diabetic vascular disease (Nishikawa et al., Nature 2000; 404:787-790). Hyperglycemia and the oxidative milieu created as a result of glucose autooxidation results in the formation of advanced glycation end-products (AGEs) (Ohgami et al., J Diabetes Complic 2002; 16:56-59) and modified low density lipoproteins (ox-LDL) (Steinberg D J Biol Chem 1997;272:20963-6) which can stimulate the production of multiple inflammatory cytokines implicated in the pathological and morphological changes found in diabetic vascular disease. The oxidation hypothesis is supported by experimental animal data in which antioxidants such as vitamin E have been demonstrated to markedly retard the atherosclerotic process (Williams et al Atherosclerosis 1992; 94: 153-59). However, despite the promising results of in vitro and laboratory studies, several recent, large scale prospective placebo-controlled trials have failed to provide conclusive evidence supporting the benefits of either vitamin E alone (HOPE Study Investigators NE J Med 2000; 342: 154-160; Hodis et al, Circulation 2002; 106: 1453-59; Jiang et al, J Biol Chem 2002; 277: 31850-6) nor in combination with other antioxidant vitamins (GISSI, Lancet 1999; 354:4477-55; Brown et al NE J Med 2001;345: 1538-92; Marchioli et al, Lipids; 2001: 36 Suppl:S53-63; Waters et al, JAMA 2002; 288:2432-40; Witztum et al Trends Cardio Med 2001;11:93-102) reduces the incidence of major adverse cardiovascular events. The Heart Outcomes Prevention Evaluation (HOPE) trial was one such study which specifically addressed the efficacy of vitamin E therapy in preventing diabetic CVD (HOPE Study Investigators NE J Med 2000; 342: 154-160). The HOPE study failed to demonstrate any clinical benefit on cardiovascular (CV) outcomes with the daily administration of 400 IU vitamin E for 4.5 years. Several mechanisms have been proposed to explain the apparent failure of vitamin E in these studies. Steinberg has proposed that benefit from antioxidant therapy may only be demonstratable in specific patient subgroups experiencing increased oxidative stress (Steinberg et al Circulation 2002; 105:2107-111).

Vascular complications occur over time in diabetics, even though their blood sugar levels may be controlled by insulin or oral hypoglycaemics (blood glucose lowering) medications. There are a number of vascular complications that diabetics are at risk of developing, including diabetic retinopathy, diabetic cataracts and glaucoma, diabetic nephropathy, diabetic neuropathy, claudication, and gangrene, hyperlipidaemia and cardiovascular problems such as hypertension, atherosclerosis and coronary artery disease. Atherosclerosis may cause angina and heart attacks, and is twice as common in people with diabetes than in those without diabetes, affecting both men and women equally.

A growing body of evidence indicates that such diabetic vascular disease develops only in those patients who are genetically susceptible (UK Prospective Study Group Diab Care 1998;21:1271-77). The haptoglobin gene is polymorphic with two major classes of alleles, denoted 1 and 2. It has been recently demonstrated that this polymorphism in the haptoglobin gene is an independent risk factor for CVD in the diabetic individual (see U.S. Pat. No. 6,613,519, to Levy et al, issued Sep. 2, 2003, Example I hereinbelow, and Levy et al J Am Coll Card 2002; 40: 1984-90). Diabetic patients homozygous for the haptoglobin 2 allele were found to have a 5 fold greater risk of CVD as compared to those homozygous for the haptoglobin 1 allele. The same authors have also demonstrated that the haptoglobin 2 allele protein product is an inferior antioxidant as compared to the haptoglobin 1 allele protein product (Melamed-Frank et al Blood 2001; 98:3693-98). However, the above-mentioned studies neither sought, nor implied, a correlation between antioxidant supplementation and CVD in diabetic patients, and the haptoglobin phenotype, or the usefulness of such a correlation in prediction of benefit to be derived from antioxidant therapy. Therefore, we hypothesized that antioxidant supplementation in diabetic patients homozygous for the haptoglobin 2 allele would be beneficial in preventing adverse cardiovascular events. In order to test this hypothesis we haptoglobin typed participants from the HOPE study and determined the relative risk ratio of major cardiovascular endpoints for the three possible haptoglobin types according to vitamin E and ramipril treatment.

There is a widely recognized need for, and it would be highly advantageous to have a method to predict which specific DM patients have lower risk with respect to cardiovascular disease, and which specific subgroup of patients would benefit from preventative antioxidant therapy. Such a method would allow medical practitioners to make best use of available resources while minimizing risk to each patient to the greatest possible extent.

SUMMARY OF THE INVENTION

According to the present invention there is provided a method of determining a potential of a diabetic patient to benefit from anti oxidant therapy for treatment of a vascular complication, the method comprising determining a haptoglobin phenotype of the diabetic patient and thereby determining the potential of the diabetic patient to benefit from said anti oxidant therapy, wherein said benefit from said anti oxidant therapy to a patient having a haptoglobin 2-2 phenotype is greater compared to patients having haptoglobin 1-2 phenotype or haptoglobin 1-1 phenotypes.

According to yet another aspect of the present invention there is provided a method of determining the importance of reducing oxidative stress in a diabetic patient so as to prevent a diabetes-associated vascular complication, the method comprising the step of determining a haptoglobin phenotype of the diabetic patient, thereby determining the importance of reducing the oxidative stress in the specific diabetic patient, wherein the importance of reducing oxidative stress is greater in a patient having a haptoglobin 2-2 phenotype compared to patients having haptoglobin 1-2 phenotype or haptoglobin 1-1 phenotypes.

According to further features in preferred embodiments of the invention described below, the vascular complication is selected from the group consisting of a microvascular complication and a macrovascular complication.

According to yet further features in preferred embodiments of the invention described below, the vascular complication is a macrovascular complication selected from the group consisting of chronic heart failure, cardiovascular death, stroke, myocardial infarction and coronary angioplasty associated restenosis.

According to still further features in preferred embodiments of the invention described below, the microvascular complication is selected from the group consisting of diabetic retinopathy, diabetic nephropathy and diabetic neuropathy.

According to further features in preferred embodiments of the invention described below, the macrovascular complication is selected from the group consisting of fewer coronary artery collateral blood vessels and myocardial ischemia.

According to yet further features in preferred embodiments of the invention described below, determining the haptoglobin phenotype is effected by determining a haptoglobin genotype of the diabetic patient.

According to still further features in preferred embodiments of the invention described below, the step of determining the haptoglobin genotype of the diabetic patient is effected by a method selected from the group consisting of a signal amplification method, a direct detection method and detection of at least one sequence change.

According to further features in preferred embodiments of the invention described below, the signal amplification method amplifies a molecule selected from the group consisting of a DNA molecule and an RNA molecule.

According to yet further features in preferred embodiments of the invention described below, the signal amplification method is selected from the group consisting of PCR, LCR (LAR), Self-Sustained Synthetic Reaction (3SR/NASBA) and Q-Beta (Qβ) Replicase reaction.

According to still further features in preferred embodiments of the invention described below, the direct detection method is selected from the group consisting of a cycling probe reaction (CPR) and a branched DNA analysis.

According to further features in preferred embodiments of the invention described below, the detection of at least one sequence change employs a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis and Dideoxy fingerprinting (ddF).

According to yet further features in preferred embodiments of the invention described below, the determining said haptoglobin phenotype is effected by directly determining the haptoglobin phenotype of the diabetic patient.

According to still further features in preferred embodiments of the invention described below, the step of determining the haptoglobin phenotype is effected by an immunological detection method.

According to further features in preferred embodiments of the invention described below, the immunological detection method is selected from the group consisting of a radioimmunoassay (RIA), an enzyme linked immunosorbent assay (ELISA), a western blot, an immunohistochemical analysis, and fluorescence activated cell sorting (FACS).

DESCRIPTION OF THE PREFERRED EMBODIMENTS

The present invention is of a method of assessing the risk of hyperglycemic patients to develop cardiovascular disease, so as to allow for preventive medicine to be practiced where applicable. Specifically, the present invention is of a method of evaluating a potential of a diabetic patient to benefit from anti-oxidant therapy for prevention of cardiovascular disease (CVD).

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Based on several large recently published large clinical trials, antioxidant therapy cannot be recommended for preventing adverse CV outcomes in patients at high risk for CVD (The Heart Outcomes Prevention Evaluation Study Investigators. N Eng J Med 2000; 342: 154-160; Hodis, et al. Circulation 2002; 106: 1453-1459; Gruppo Italiano per lo Studio della Sopravvivenza nell'Infarto Miocardico. Lancet 1999; 354: 447-455; Brown et al. N Engl J Med 2001; 345: 1583-1592.)

However, these studies could not rule out potential benefit to a subset of these patients (Steinberg D, Witzum J L. Circulation 2002; 105; 2107-2111). While analyzing data from a large study of the efficacy of preventive antioxidant therapy, which failed to indicate any benefit from antioxidant therapy for the entire sample, the present authors have, for the first time, demonstrated that a subgroup can be identified which did benefit from antioxidant supplementation. Specifically, diabetic individuals in the HOPE study having a Hp 2-2 phenotype had a statistically significant reduction in CV death and non-fatal myocardial infarction with vitamin E supplementation and a statistically significant reduction in the composite endpoint (non-fatal MI, stroke or cardiovascular death) with ramipril therapy (see Example II hereinbelow). Analysis of the correlation between haptoglobin phenotype and CVD in the Strong Heart Study indicates that patients with Hp 2-2 are at increased risk for diabetic CVD (see Example I hereinbelow, and Levy A P et al. J Am Coll Card 2002; 40: 1984-1990) and that Hp 2-2 is an inferior antioxidant (Melamed-Frank M, et al. Blood 2001; 98: 3693-3698). Without wishing to be limited by a single hypothesis, the inferior antioxidant properties of Hp 2-2 may explain why benefit from antioxidants may be selectively derived in this subgroup of diabetic patients and that these findings are clearly statistically significant. Further support for such an effect of haptoglobin can be found in the fact that no significant effect of the haptoglobin type on the incidence of CVD in patients without diabetes has been observed (see Example I hereinbelow), nor has any effect of antioxidant therapy (with vitamin E) in non-diabetic patients been shown (see Example II hereinbelow). Without wishing to be limited by a single hypothesis, it can be hypothesized that the importance of the decreased antioxidant activity of Hp 2-2 is only manifested clinically in the presence of an additional mechanism producing oxidative stress (diabetes).

Thus, according to the present invention there is provided a method of determining a potential of a diabetic patient to benefit from anti oxidant therapy for treatment of a vascular complication, the method comprising determining a haptoglobin phenotype of the diabetic patient and thereby determining the potential of the diabetic patient to benefit from said anti oxidant therapy, wherein said benefit from said anti oxidant therapy to a patient having a haptoglobin 2-2 phenotype is greater compared to patients having haptoglobin 1-2 phenotype or haptoglobin 1-1 phenotypes.

Whereas the results of studies such as the HOPE and GISSI study failed to provide any indication of subpopulations for whom antioxidant therapy is effective, the data presented herein clearly show, for the first time, that diabetic individuals having a Hp 2-2 phenotype had a statistically significant reduction in CV death and non-fatal myocardial infarction with vitamin E supplementation and a statistically significant reduction in the composite endpoint (non-fatal MI, stroke or cardiovascular death) with ramipril therapy (see Example II hereinbelow). Thus, the present invention further provides a method of determining the importance of reducing oxidative stress in a diabetic patient so as to prevent a diabetes-associated vascular complication, the method comprising the step of determining a haptoglobin phenotype of the diabetic patient, thereby determining the importance of reducing the oxidative stress in the specific diabetic patient, wherein said importance of reducing oxidative stress is greater in a patient having a haptoglobin 2-2 phenotype compared to patients having haptoglobin 1-2 phenotype or haptoglobin 1-1 phenotypes.

The present invention also provides a kit for evaluating the potential of a diabetic patient to benefit from anti oxidant therapy for treatment of a vascular complication. The kit comprises packaged reagents for determining a haptoglobin phenotype of the diabetic patient and the kit is identified for use in evaluating a potential of a diabetic patient to benefit from anti oxidant therapy for treatment of a vascular complication. The nature of these reagents will become apparent to those of skill in the art from the following descriptions and further from well known and characterized sequence data of the haptoglobin 1 and 2 alleles.

The utility of the methods and kit of the invention is demonstrated by data presented in Tables 1-6 of the Examples section that follows.

Thus, it is demonstrated herein, in a sample from of a population-based longitudinal study, that the haptoglobin phenotype is a significant predictor of the potential of a diabetic patient to benefit from anti oxidant therapy for treatment of a vascular complication. In one embodiment of the present invention, the vascular complication is selected from the group consisting of a microvascular complication and a macrovascular complication.

There are a number of vascular complications that diabetics are at risk of developing, including diabetic retinopathy, diabetic cataracts and glaucoma, diabetic nephropathy, diabetic neuropathy, claudication, and gangrene, hyperlipidaemia and cardiovascular problems such as hypertension, atherosclerosis and coronary artery disease. Atherosclerosis may cause angina and heart attacks, and is twice as common in people with diabetes than in those without diabetes, affecting both men and women equally. As used herein, the microvascular complications of diabetes include diabetic neuropathy (nerve damage), diabetic nephropathy (kidney disease) and vision disorders (eg diabetic retinopathy, glaucoma, cataract and corneal disease). Macrovascular complications include accelerated atherosclerotic coronary vascular conditions such as myocardial infarct, chronic heart failure, cardiovascular death and heart disease, stroke and peripheral vascular disease (which can lead to ulcers, gangrene and amputation).

In a further embodiment, the vascular complication is a macrovascular complication selected from the group consisting of chronic heart failure, cardiovascular death, stroke, myocardial infarction, coronary angioplasty associated restenosis, fewer coronary artery collateral blood vessels and myocardial ischemia. In another embodiment, the vascular complication is a microvascular complication, such as diabetic neuropathy, diabetic nephropathy or diabetic retinopathy The predictive value of haptoglobin for potential benefit from antioxidant supplementation for vascular conditions in diabetics is further supported by the correlation between the frequency of the haptoglobin 1 allele in different ethnic groups and the relative incidence of diabetic microvascular and macrovascular complications in these groups.

For example, African-Caribbeans with diabetes have a low relative risk of CVD[4,16] and microvascular complications and have a high frequency of the haptoglobin 1 allele (as high as 0.87 in some populations)[26] while diabetic Australian-Aborigines[19] and South Asian[12,15] peoples with diabetes have a high relative risk of CVD and diabetic microvascular[47] complications and a relatively low frequency of the haptoglobin 1 allele (0.18 and 0.09, respectively).[26]

Two mechanisms by which haptoglobin phenotype may influence the clinical course of atherosclerotic CVD were recently identified. First, a graded risk of restenosis after percutaneous transluminal coronary artery angioplasty was demonstrated to be related to the number of haptoglobin 2 alleles.[27,30] Second, it was demonstrated that diabetic individuals with the haptoglobin 2-1 phenotype are significantly more likely to have coronary artery collaterals as compared to individuals with the haptoglobin 2-2 phenotype with a similar degree of coronary artery disease. Inter-individual differences in the extent of the coronary collateral circulation have previously been demonstrated to be a key determinant of the extent of a myocardial infarction.[48]

Several functions have been assigned to the haptoglobin protein that may impact on the development of atherosclerosis. It has been appreciated for over 60 years that a major function of serum haptoglobin is to bind free hemoglobin.[22] This interaction is thought to help scavenge iron and prevent its loss in the urine and to serve as an antioxidant thereby protecting tissues against hemoglobin mediated tissue oxidation.[23] The antioxidant capacity of the different haptoglobin phenotypes has been shown to differ with the haptoglobin 1-1 protein appearing to confer superior antioxidant protection as compared to the other forms of the protein.[23] Such an antioxidant hypothesis is particularly intriguing given the apparent important role of oxidative stress in the development of diabetic vascular complications.[49,50] Perhaps further amplifying apparent differences in the oxidative protection afforded by the different types of haptoglobin are gross differences in size of the haptoglobin protein present in individuals with the different phenotypes. Haptoglobin 1-1 is markedly smaller then haptoglobin 2-2 and thus may be better able to sieve into the extravascular compartment and prevent hemoglobin mediated tissue damage at sites of vascular injury.[23] Nonetheless, the role of haptoglobin in atherosclerosis is still poorly understood, with some studies paradoxically demonstrating that Hp 1-1 confers elevated risk of cardiovascular mortality (De Bacquer et al, Atherosclerosis 2001; 157:161-6).

Haptoglobin has also been demonstrated to play a role as an immunomodulator that may not be unrelated to its role in hemoglobin metabolism.[21,23] A specific receptor for the haptoglobin-hemoglobin complex has recently been definitively identified on monocyte/macrophages as CD16351, a member of the group B scavenger receptor cysteine-rich superfamily.[52] Another member of this superfamily of scavenger receptors, CD36, has previously been shown to play an important role in LDL metabolism with profound significance for the development of atherosclerotic lesions.[53-55] Haptoglobin 2-2 complexed to hemoglobin was found to have a 10 fold higher affinity for this receptor than haptoglobin 1-1 complexed to hemoglobin.[51] Ligand binding to CD 163 has been shown to induce a tyrosine-kinase dependent signal cascade resulting in secretion of a number of inflammatory cytokines.[56] Haptoglobin alone has also been demonstrated to bind to granulocytes and monocytes. Haptoglobin appears to block the neutrophil response to a variety of agonists with defined plasma membrane receptors suggesting that it may serve as an antagonist for receptor-ligand interaction of the immune system.[57] Specific binding of haptoglobin has been demonstrated to the MAC-1 or CD11 b/CD18 receptor[58], a member of the integrin family. These integrins have been shown to play a major role in the response of the vessel wall to injury.[59]

An important role of bacterial infection in the development and destabilization of the atherosclerotic plaque has recently been suggested by many investigations.[60] In this regard it may be of importance vis-a-vis the differential risk of atherosclerosis associated with haptoglobin phenotype that the phenotypes appear to differ in their ability to prevent bacterial and viral replication in vitro and in vitro.[23-25] This may be due to differences in iron scavenging[23] as well as to differences in immunoregulation afforded by the different phenotypes.[51]

These findings are in complete agreement with the results presented herein regarding the haptoglobin phenotype and the benefits derived from antioxidant supplementation for prevention of diabetic vascular complications. The marked differences in the relative response of diabetic patients having different haptoglobin phenotypes to antioxidant therapy would appear to warrant wide scale testing of diabetic patients to be used in CVD risk stratification algorithms and in evaluation of potential therapeutic interventions designed to prevent CVD in the diabetic patient, such as antioxidant supplementation and combined antioxidant and pharmacological therapy.

According to various preferred embodiments of the method of the present invention, determining the haptoglobin phenotype of a testee is effected by any one of a variety of methods including, but not limited to, a signal amplification method, a direct detection method and detection of at least one sequence change. These methods determine a phenotype indirectly, by determining a genotype. As will be explained hereinbelow, determination of a haptoglobin phenotype may also be accomplished directly by analysis of haptoglobin gene products.

The signal amplification method according to various preferred embodiments of the present invention may amplify, for example, a DNA molecule or an RNA molecule. Signal amplification methods which might be used as part of the present invention include, but are not limited to PCR, LCR (LAR), Self-Sustained Synthetic Reaction (3SR/NASBA) or a Q-Beta (Qβ) Replicase reaction.

Polymerase Chain Reaction (PCR): The polymerase chain reaction (PCR), as described in U.S. Pat. Nos. 4,683,195 and 4,683,202 to Mullis and Mullis et al., is a method of increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves the introduction of a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization (annealing), and polymerase extension (elongation) can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

Ligase Chain Reaction (LCR or LAR): The ligase chain reaction [LCR; sometimes referred to as "Ligase Amplification Reaction" (LAR)] described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method of amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, and ligation amplify a short segment of DNA. LCR has also been used in combination with PCR to achieve enhanced detection of single-base changes. Segev, PCT Publication No. W09001069 A1 (1990). However, because the four oligonucleotides used in this assay can pair to form two short ligatable fragments, there is the potential for the generation of target-independent background signal. The use of LCR for mutant screening is limited to the examination of specific nucleic acid positions.

Self-Sustained Synthetic Reaction (3SR1NASBA): The self-sustained sequence replication reaction (3SR) (Guatelli et al., Proc. Natl. Acad. Sci., 87:1874-1878, 1990), with an erratum at Proc. Natl. Acad. Sci., 87:7797, 1990) is a transcription-based in vitro amplification system (Kwok et al., Proc. Natl. Acad. Sci., 86:1173-1177, 1989) that can exponentially amplify RNA sequences at a uniform temperature. The amplified RNA can then be utilized for mutation detection (Fahy et al., PCR Meth. Appl., 1:25-33, 1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200-300 base pairs).

Q-Beta (Qβ) Replicase: In this method, a probe which recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37 degrees C.). This prevents the use of high temperature as a means of achieving specificity as in the LCR, the ligation event can be used to detect a mutation at the junction site, but not elsewhere.

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55 degrees C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

The basis of the amplification procedure in the PCR and LCR is the fact that the products of one cycle become usable templates in all subsequent cycles, consequently doubling the population with each cycle. The final yield of any such doubling system can be expressed as: $(1+X)^n=y$, where "X" is the mean efficiency (percent copied in each cycle), "n" is the number of cycles, and "y" is the overall efficiency, or yield of the reaction (Mullis, PCR Methods Applic., 1:1, 1991). If every copy of a target DNA is utilized as a template in every cycle of a polymerase chain reaction, then the mean efficiency is 100%. If 20 cycles of PCR are performed, then the yield will be $2^{20}$, or 1,048,576 copies of the starting material. If the reaction conditions reduce the mean efficiency to 85%, then the yield in those 20 cycles will be only $1.85^{20}$, or 220,513 copies of the starting material. In other words, a PCR running at 85% efficiency will yield only 21% as much final product, compared to a reaction running at 100% efficiency. A reaction that is reduced to 50% mean efficiency will yield less than 1% of the possible product.

In practice, routine polymerase chain reactions rarely achieve the theoretical maximum yield, and PCRs are usually run for more than 20 cycles to compensate for the lower yield. At 50% mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator. The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method of the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al., Nucl. Acids Res., 18:999, 1990)

A similar 3'-mismatch strategy is used with greater effect to prevent ligation in the LCR (Barany, PCR Meth. Applic., 1:5, 1991). Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

The direct detection method according to various preferred embodiments of the present invention may be, for example a cycling probe reaction (CPR) or a branched DNA analysis.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern band RNase protection assays usually require the use of radioactivity and are not amenable to automation. Recently devised techniques have sought to eliminate the use of radioactivity and/or improve the sensitivity in automatable formats. Two examples are the "Cycling Probe Reaction" (CPR), and "Branched DNA" (bDNA).

Cycling probe reaction (CPR): The cycling probe reaction (CPR) (Duck et al., BioTech., 9:142, 1990), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Branched DNA: Branched DNA (bDNA), described by Urdea et al., Gene 61:253-264 (1987), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

The detection of at least one sequence change according to various preferred embodiments of the present invention may be accomplished by, for example restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis or Dideoxy fingerprinting (ddF).

The demand for tests which allow the detection of specific nucleic acid sequences and sequence changes is growing rapidly in clinical diagnostics. As nucleic acid sequence data for genes from humans and pathogenic organisms accumulates, the demand for fast, cost-effective, and easy-to-use tests for as yet mutations within specific sequences is rapidly increasing.

A handful of methods have been devised to scan nucleic acid segments for mutations. One option is to determine the entire gene sequence of each test sample (e.g., a bacterial isolate). For sequences under approximately 600 nucleotides, this may be accomplished using amplified material (e.g., PCR reaction products). This avoids the time and expense associated with cloning the segment of interest. However, specialized equipment and highly trained personnel are required, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Restriction fragment length polymorphism (RFLP): For detection of single-base differences between like sequences, the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis).

Single point mutations have been also detected by the creation or destruction of RFLPs. Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), Nucleic Acids and Molecular Biology, vol. 2, Springer-Verlag, Heidelberg, 1988). Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, Trends Genet., 3:167, 1987). Recently, endonucleases encoded by group I introns have been discovered that might have greater than 12 base-pair specificity (Perhnan and Butow, Science 246:1106, 1989), but again, these are few in number.

Allele specific oligonucleotide (ASO): If the change is not in a recognition sequence, then allele-specific oligonucleotides (ASOs), can be designed to hybridize in proximity to the mutated nucleotide, such that a primer extension or ligation event can bused as the indicator of a match or a mismatch. Hybridization with radioactively labeled allelic specific oligonucleotides (ASO) also has been applied to the detection of specific point mutations (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles. The ASO approach applied to PCR products also has been extensively utilized by various researchers to detect and characterize point mutations in ras genes (Vogelstein et al., N. Eng. J. Med., 319:525-532, 1988; and Farr et al., Proc. Natl. Acad. Sci., 85:1629-1633, 1988), and gsp/gip oncogenes (Lyons et al., Science 249:655-659, 1990). Because of the presence of various nucleotide changes in multiple positions, the ASO method requires the use of many oligonucleotides to cover all possible oncogenic mutations.

With either of the techniques described above (i.e., RFLP and ASO), the precise location of the suspected mutation must be known in advance of the test. That is to say, they are inapplicable when one needs to detect the presence of a mutation within a gene or sequence of interest.

Denaturing/Temperature Gradient Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of mutations in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475, 1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA:RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of mutations.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

According to a presently preferred embodiment of the present invention the step of searching for the mutation or mutations in any of the genes listed above, such as, for example, the reduced folate carrier (RFC) gene, in tumor cells or in cells derived from a cancer patient is effected by a single strand conformational polymorphism (SSCP) technique, such as cDNA-SSCP or genomic DNA-SSCP. However, alternative methods can be employed, including, but not limited to, nucleic acid sequencing, polymerase chain reaction, ligase chain reaction, self-sustained synthetic reaction, Qβ-Replicase, cycling probe reaction, branched DNA, restriction fragment length polymorphism analysis, mismatch chemical cleavage, heteroduplex analysis, allele-specific oligonucleotides, denaturing gradient gel electrophoresis, constant denaturant gel electrophoresis, temperature gradient gel electrophoresis and dideoxy fingerprinting.

Determination of a haptoglobin phenotype may, as if further exemplified in the Examples section that follows, also be accomplished directly, by analyzing the protein gene products of the haptoglobin gene, or portions thereof. Such a direct analysis is often accomplished using an immunological detection method.

Immunological detection methods are fully explained in, for example, "Using Antibodies: A Laboratory Manual" (Ed Harlow, David Lane eds., Cold Spring Harbor Laboratory Press (1999)) and those familiar with the art will be capable of implementing the various techniques summarized hereinbelow as part of the present invention. All of the immunological techniques require antibodies specific to at least one of the two haptoglobin alleles. Immunological detection methods suited for use as part of the present invention include, but are not limited to, radio-immunoassay (RIA), enzyme linked immunosorbent assay (ELISA), western blot, immunohistochemical analysis, and fluorescence activated cell sorting (FACS).

Radio-immunoassay (RIA): In one version, this method involves precipitation of the desired substrate, haptoglobin in this case and in the methods detailed hereinbelow, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, A labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a calorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

While reducing the present invention to practice, analysis of the data of the HOPE study has also uncovered, for the first time, a similar haptoglobin-type specific benefit for vitamin E and for the drug ramipril. Ramipril is commonly prescribed for hypertension, and a such could be expected to contribute to the prevention of CVD. However, the magnitude of the preventive effect of ramipril treatment (RR=0.57) and the strict restriction of prevention to one haptoglobin phenotype subgroup (Hp 2-2) indicates a preventive component of ramipril therapy beyond it's effect on hypertension. In addition to its activity as an angiotensin converting enzyme (ACE) inhibitor, ramipril has activity as an antioxidant as therapy with ramipril results in a reduction of free radical oxidative species in vivo (Lopez-Jaramillo, et al J Hum Hypertens 2002; 16S1:S100-300). The demonstration here that two different antioxidants with dramatically different biochemical structures provide similar clinical benefit to a subgroup of diabetic patients identified by haptoglobin typing suggests that the anti-oxidant therapy paradigm may be applied for other antioxidants as well such as Trolox (Sagach et al Pharma Res 202;45:435-39), Raxofelast (Campo et al, Cardiovasc Drug Rev 1997; 15:157-73), TMG (Meng et al Bioorg Med Chem Ltrs 2002;12:2545-48); AGI-1067 (Yoshida et al Atheroscler 2002; 162: 111-17), Probucol (Kita et al PNAS USA 1987; 84:7725), as well as calcium channel blockers (Mak I, et al. Pharma Res. 2002;45:27-33) such as nisoldapine, nifedipine and nicardipine having a similar mechanism of antioxidant action to that of vitamin E. Thus, the patient population in whom preventative therapy with such antioxidants would be expected to be most beneficial (diabetics with Hp 2-2) would be similar to that demonstrated here to derive a benefit from vitamin E and ramipril supplementation. However, determination of benefits to be derived from antioxidant supplementation in DM patients may not be applicable to all antioxidant vitamins, since no correlation could be found between CVD outcomes and Vitamin C supplementation, either in unselected samples or in Diabetic patients (data not shown).

The novel approach to analysis of the HOPE study data presented herein has now provided clear evidence that whereas there is no apparent benefit of the antioxidant vitamin E in a non-stratified population of diabetic patients, a subgroup of diabetic patients can identified in whom antioxidant therapy demonstrates significant benefit. Thus, these data indicate the enormous value of haptoglobin phenotyping for all diabetic patients and provision of preventative antioxidant supplement therapy for patients with Hp 2-2 phenotype, in order to prevent diabetic CVD. It is likely that this preventative antioxidant effect is not limited to a single antioxidant (such as Vitamin E) and a that variety of potential antioxidants, such as Trolox, Raxefilofast, AGI-1067, Probucol, TMG and calcium channel blockers are also effective. The relative efficacy of these different agents can be determined from analysis of further clinical studies.

It will be appreciated by one ordinarily skilled in the art that determining the haptoglobin phenotype of an individual, either directly or genetically, may be effected using any suitable biological sample derived from the examined individual, including, but not limited to, blood, plasma, blood cells, saliva or cells derived by mouth wash, and body secretions such as urine and tears, and from biopsies, etc.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Methods

Before presenting examples which provide experimental data to support the present invention, reference is made to the following methods:

Patients:

Detailed descriptions of the Strong Heart Study design, survey methods and laboratory techniques and the participating Indian communities have been previously published.[20,39,40]

The study cohort consists of over 4,549 individuals aged 45 to 74 who were seen at the first examination conducted between July 1989 and January 1992. Participation rates of all eligible tribe members averaged 64%. Non-participants were similar to participants in age and self reported frequency of diabetes. Reexamination rates for those alive at the second examination (July 1993 to December 1995) averaged 88% and at the third examination (July 1997 to December 1999) averaged 90%.

The clinical examination at each phase consisted of a personal interview and a physical examination. Fasting blood samples were taken for biochemical measurements and a 75 grams oral glucose tolerance test was performed. Blood samples were collected in the presence of EDTA, the plasma was harvested and stored at −20° C. Standardized blood pressure measurements were obtained and electrocardiograms were recorded and coded as previously described.[39,40] Participants were classified as diabetic according to World Health Organization criteria.[41] Participants were considered hypertensive if they were taking anti-hypertensive medications or if they had a systolic blood pressure greater than 140 mm Hg or a diastolic blood pressure of greater than 90 mm Hg.

Deaths among the Strong Heart Study cohort between 1988 and the present were identified through tribal and hospital records and by direct contact by study personnel with participants and their families. Copies of death certificates were obtained from state health departments and ICD-9 coded centrally by a nosologist. Possible CVD deaths were initially identified from death certificates as described previously.[42] Cause of death was investigated through autopsy reports, medical records abstractions, and informant interviews as described previously.[42] All materials were reviewed independently by physician members of the Strong Heart Study Mortality Review Committee to confirm the cause of death. Criteria for fatal CVD and stroke were as described previously.[42]

Medical records were reviewed at each examination to identify any nonfatal cardiovascular events, definite MI and definite CVD as previously described[20,43], that had occurred since the previous examination. Records of those who did not participate in the second or third examination were also reviewed. For all potential CVD events or interventions, medical records were reviewed by trained medical record abstractors. Records of outpatient visits were reviewed and abstracted for procedures diagnostic of CVD (e.g., treadmill test, coronary angiography). Information obtained from chart review was reviewed by a physician member of the Strong Heart Study mortality or morbidity review committee to establish the specific CVD diagnosis. Blinded review of the abstracted records by other physician members of the Morbidity Review Committee showed >90% concordance in the diagnosis.

HOPE study and patient characteristics: The Heart Outcomes Prevention Evaluation (HOPE) study was designed to test the hypotheses that two preventive intervention strategies, namely angiotensin-converting enzyme (ACE) inhibition or vitamin E, would improve morbidity and mortality in patients at high risk of cardiovascular events compared with placebo. Patients were included in the study who were considered to be at high risk of future fatal or non-fatal cardiovascular events, by virtue of their age (>55 years), existing or previous cardiovascular disease, or diabetes. Diabetics had at least one other risk factor, either known vascular disease or other factors such as cigarette smoking, high cholesterol or hypertension. Ramipril or placebo was added to concomitant medication, which included, in a substantial proportion of patients, antihypertensive drugs (excluding ACE-I), lipid-lowering agents or aspirin. The HOPE study design and protocols have been previously described in detail (see, for example, The Heart Outcomes Prevention Evaluation Study Investigators NE J Med, 2000; 342:154-60 and Sleight, P, J Rennin Angioten Aldost Sys 2000;1:18-20). Briefly, the study population consisted over 9,451 patients at high risk of CVD (3,654 DM). The study had a 2×2 factorial design with randomization to 400IU natural source vitamin E (RRR-a-tocophorol acetate) or placebo and to 10 mg of ramipril or placebo. Patients were followed for a mean of 4.5 years. The primary study outcome was the composite of non-fatal MI, stroke or cardiovascular death.

Definition of Case and Controls:

The present study is a case-control sample designed to examine the relationship between CVD and haptoglobin phenotype. 206 CVD cases and controls (matched for age, gender and geographic area) were subjected to this analysis.

Haptoglobin Phenotyping:

Haptoglobin phenotyping was determined from 10 µl of EDTA-plasma by gel electrophoresis and peroxidase staining using a modification[44,45] of the method originally described by Smithies[46] which used starch gel electrophoresis and peroxidase staining with benzidine. Patients' plasma was stored at −20° C. All chemicals were purchased from Sigma Israel (Rehovot, Israel). A 10% hemoglobin solution in water was prepared from heparinized blood by first washing the blood cells 5 times in phosphate buffered saline and then lysing the cells in 9 ml of sterile water per ml of pelleted cell volume. The cell lysate was centrifuged at 10,000 g for 40 minutes and the supernatant containing hemoglobin was aliquoted and stored at −70° C. Serum (10 µl) was mixed with 2 µl of the 10% hemoglobin solution and the samples permitted to stand for 5 minutes at room temperature in order to allow the haptoglobin-hemoglobin complex to form. An equal volume (12 µl) of sample buffer containing 125 mM Tris Base pH 6.8, 20% (w/v) glycerol and 0.001% (w/v) bromophenol blue was added to each sample prior to running on the gel. The haptoglobin hemoglobin complex was resolved by polyacrylamide gel electrophoresis using a buffer containing 25 mM Tris Base and 192 mM glycine. The stacking gel was 4% polyacrylamide (29:1 acrylamide/bis-acrylamide) in 125 mM Tris Base, pH 6.8 and the separating gel was 4.7% polyacrylamide (29:1 acylamidelbis-acrylamide) in 360 mM Tris Base, pH 8.8. Electrophoresis was performed at a constant voltage of 250 volts for 3 hours. After the electrophoresis was completed the haptoglobin-hemoglobin complexes were visualized by soaking the gel in freshly prepared staining solution in a glass tray. The staining solution (prepared by adding the reagents in the order listed) contained 5 ml of 0.2% (w/v) 3,3',5,5'-tetramethylbenzidine in methanol, 0.5 ml dimethylsulfoxide, 10 ml of 5% (v/v) glacial acetic acid, 1 ml of 1% (w/v) potassium ferricyanide and 150 µl of 30% (w/w) hydrogen peroxide. The bands corresponding to the haptoglobin-hemoglobin complex were readily visible within 15 minutes and were stable for over 48 hours. All gels were documented with photographs. The haptoglobin phenotype of all samples was determined at the laboratory without any knowledge concerning the patient.

Plasma samples were received by the laboratory for analysis and haptoglobin phenotyping was possible on all but six of these samples. For these six patients it is not clear if they represent patients who do not make any haptoglobin (Hp 0 phenotype)[22,23] or that the haptoglobin concentration is below the detection limit for the assay described.

For samples from the HOPE Study, haptoglobin phenotyping was performed from 10 ul of plasma by polyacrylamide gel electrophoresis according to established methods (Hochberg I et al Atherosclerosis 2002;161:441-446). A signature banding pattern is obtained from individuals who are homozygous for the 1 allele (Hp 1-1), homozygous for the 2 allele (Hp 2-2) or who are heterozygous at the haptoglobin locus (Hp 2-1). We have established 100% concordance between the haptoglobin phenotype as determined from plasma and the haptoglobin genotype as determined from genomic DNA by the polymerase chain reaction (Koch W, et al Clin Chem 2002; 277:13635-40). An unambiguous haptoglobin phenotype was obtained on greater than 99.6% of all samples assayed. Haptoglobin phenotyping was performed with no knowledge of the patients clinical or treatment status.

Statistical Analysis:

CVD risk factors of age, gender, LDL and HDL cholesterol, triglycerides, systolic BP, BMI, diabetes, smoking status, family history of CVD and recruitment center were compared between cases and controls as well as between the three haptoglobin phenotypes. In addition DM characteristics consisting of insulin, fasting glucose levels, HbAlc, DM duration and family history of DM were compared between cases and controls as well as between the three haptoglobin phenotypes. Univariate and multinomial logistic regression modeling was performed to determine if these CVD risk factors and DM characteristics were related to phenotype. The likelihood ratio was used to test parameters.

A conditional logistic regression model was run modeling the probability of having a CVD event for a diabetic patient by the three haptoglobin phenotypes adjusting for the CVD risk factors and the DM characteristics. The diabetes-phenotype interaction was coded using two indicator variables, one for patients with diabetes and another for patients without diabetes. Model fit was assessed by an analysis of residuals.

All analyses of the HOPE Study data were carried out using SAS 6.02. Baseline characteristics of patients according to haptoglobin were compared by t tests or $\chi 2$ tests as appropriate. Relative risks (RRs) and 95% confidence intervals are reported for the primary outcomes of cardiovascular death, non-fatal myocardial infarction, and stroke.

Experimental Results

Example I

Haptoglobin Phenotype is Predictive of Risk of CVD in Diabetic Patients

The clinical characteristics of the case control cohort according to CVD risk factors and DM characteristics is shown in Table 1 below.

TABLE 1

CVD Risk Factors by Case-Control Status

| CVD Risk Factors | | Controls | | | Cases | | |
|---|---|---|---|---|---|---|---|
| | | Mean | STD | | Mean | STD | |
| Age | | 59.16 | 8.01 | | 60.09 | 8.08 | |
| LDL Cholesterol | | 112.1 | 30.44 | | 123.0 | 40.47 | |

| | Median | Min | Max | Median | Min | Max |
|---|---|---|---|---|---|---|
| DM duration | | | | 6.00 | 0.00 | 41.00 |
| Systolic BP | 124.0 | 81.00 | 210.0 | 131.0 | 88.00 | 205.0 |
| BMI | 29.76 | 17.71 | 48.07 | 29.84 | 19.59 | 72.36 |
| HbA1c | 4.00 | 4.00 | 13.10 | 7.20 | 4.00 | 15.50 |
| Fasting Glucose | 118.5 | 77.00 | 365.0 | 148.0 | 57.00 | 354.0 |
| Insulin | 15.99 | 2.20 | 144.7 | 18.45 | 1.50 | 314.5 |

| | | n | % | n | % |
|---|---|---|---|---|---|
| Female Gender | | 102 | 49.51 | 102 | 49.51 |
| Diabetes | | 93 | 45.15 | 146 | 70.89 |
| Current Smoker | | 136 | 66.0 | 143 | 70.69 |
| Family hx DM | | 131 | 63.5 | 145 | 70.34 |
| Family hx CVD | | 119 | 57.77 | 148 | 71.84 |
| Center | OK | 74 | 35.92 | 74 | 35.92 |
| | SD | 73 | 35.44 | 73 | 35.44 |
| | AZ | 59 | 28.64 | 59 | 28.64 |

Cases and controls were matched for age, gender and geographic area. These data are consistent with previous finding in this population that diabetes, LDL cholesterol, and hypertension are all independent predictors of CVD.[20]

Haptoglobin phenotyping of this cohort revealed a distribution of 25% 1-1, 44% 2-1 and 31% 2-2. The frequency of the 1 allele was 0.47 which is in good agreement with haptoglobin allelic frequency for this population that has been previously reported.[26] No significant difference was found between the different haptoglobin phenotypes for any of the CVD risk factors or DM characteristics as determined both by univariate analysis and by multinomial logit regression analysis modeling the probability of having a 1-1 phenotype.

Table 2 below provides the conditional logistic regression predicting the probability of a CVD event for each of the haptoglobin phenotypes in diabetic and non-diabetic individuals prior to and after adjustment for CVD risk factors and DM characteristics.

TABLE 2

Conditional logistic regression predicting the probability of a CVD event

| Variable | OR | 95% CI | p-value |
|---|---|---|---|
| Unadjusted | | | |
| DM and Hp 2-1 (vs DM and Hp 1-1) | 2.32 | (1.27-4.23) | 0.006 |
| DM and Hp 2-2 (vs DM and Hp 1-1) | 5.08 | (2.37-10.89) | <0.001 |
| DM and Hp 2-2 (vs DM and Hp 2-1) | 3.26 | (1.67-6.37) | <0.001 |
| No DM, Hp 2-1 (vs no DM, Hp 1-1) | 0.63 | (0.33-1.20) | 0.159 |
| No DM, Hp 2-2 (vs no DM, Hp 1-1) | 1.10 | (0.53-2.30) | 0.795 |
| No DM, Hp 2-2 (vs no DM, Hp 2-1) | 0.75 | (0.40-1.38) | 0.350 |
| Adjusted for DM characteristics only | | | |
| DM and Hp 2-1 (vs DM and Hp 1-1) | 1.86 | (0.93-3.69) | 0.078 |
| DM and Hp 2-2 (vs DM and Hp 1-1) | 3.90 | (1.68-9.09) | 0.002 |
| DM and Hp 2-2 (vs DM and Hp 2-1) | 2.10 | (1.00-4.40) | 0.049 |
| No DM, Hp 2-1 (vs no DM, Hp 1-1) | 1.40 | (0.48-4.09) | 0.542 |
| No DM, Hp 2-2 (vs no DM, Hp 1-1) | 2.31 | (0.76-7.05) | 0.141 |
| No DM, Hp 2-2 (vs no DM, Hp 2-1) | 1.65 | (0.73-3.75) | 0.228 |
| Adjusted for DM characteristics and CVD risk factors | | | |
| DM and Hp 2-1 (vs DM and Hp 1-1) | 1.85 | (0.86-3.96) | 0.116 |
| DM and Hp 2-2 (vs DM and Hp 1-1) | 4.70 | (1.86-11.88) | 0.001 |
| DM and Hp 2-2 (vs DM and Hp 2-1) | 2.55 | (1.14-5.67) | 0.022 |
| No DM, Hp 2-1 (vs no DM, Hp 1-1) | 1.70 | (0.53-5.49) | 0.373 |
| No DM, Hp 2-2 (vs no DM, Hp 1-1) | 2.97 | (0.90-9.77) | 0.073 |
| No DM, Hp 2-2 (vs no DM, Hp 2-1) | 1.75 | (0.71-4.29) | 0.225 |

These data show, after adjustment for all CVD risk factors and DM characteristics, that among Strong Heart Study participants with diabetes, those with a haptoglobin phenotype of 2-2 are 4.7 (1.86-11.88 OR 95% CI) times more likely to have had a CVD event than those with a 1-1 phenotype (p=0.001) and 2.5 (1.14-5.67 OR 95% CI) times more likely to have had a CVD event than those with a 2-1 phenotype (p=0.022). Moreover, patients with a haptoglobin phenotype of 2-1 were 1.8 (0.86-3.96 OR 95% CI) times more likely to have had a CVD event than those with the 1-1 phenotype although this was not statistically significant. Taken together, these data suggest the existence of a graded risk conferred by the number of haptoglobin 2 alleles on the development of CVD in diabetic individuals.

Finally, in patients without diabetes a trend was observed of borderline statistical significance showing that the non-diabetic patients with a haptoglobin phenotype of 2-2 are 3.0 (0.90-9.77 OR 95% CI) times more likely to have had a CVD event than those non-diabetics with a 1-1 phenotype (p=0.073).

Table 3 below summarizes these results:

TABLE 3

Conditional Logistic Regression predicting the probability of a CVD event adjusted for DM and CVD risk factors

| Risk Factors | OR (of CVD) | 95% CI Lower | 95% CI Upper | p-value |
|---|---|---|---|---|
| DM and Hp 2-1 (vs dm and Hp 1-1) | 1.85 | 0.86 | 3.96 | 0.116 |
| DM and Hp 2-2 (vs dm and Hp 1-1) | 4.70 | 1.86 | 11.88 | 0.001 |
| DM and Hp 2- (vs dm and Hp 2-1) | 2.55 | 1.14 | 5.67 | .022 |
| No DM, Hp 2-1 (vs no dm, Hp 1-1) | 1.70 | 0.53 | 5.49 | 0.373 |
| No DM, Hp 2-2 (vs no dm, Hp 1-1) | 2.97 | 0.90 | 9.77 | 0.073 |
| No DM, Hp 2-2 (vs no dm, Hp 2-1) | 1.75 | 0.71 | 4.29 | 0.225 |

Example II

Haptoglobin Phenotype is Predictive of Benefit from Antioxidant Therapy in Diabetic Patients Patient characteristics of HOPE samples undergoing haptoglobin phenotyping: Haptoglobin phenotype was obtained on 3176 patients (1078 diabetics) from the original HOPE cohort for whom plasma was originally archived. These patients represented a randomly selected consecutive series of patients from the entire HOPE cohort. The clinical characteristics of the HOPE cohort according to CVD risk factors and treatment regimen is shown in Table 4 below.

TABLE 4

Patient characteristics in the HOPE Study

|  | Hp 1-1 (N = 487) | Hp 2-1 (N = 1454) | Hp 2-2 (N = 1226) |
|---|---|---|---|
| Demographic data | | | |
| Age (SD) yrs | 65.8 (6.5) | 65.4 (6.4) | 65.3 (6.7) |
| Female n (%) | 105 (21.6) | 309 (21.3) | 290 (23.7) |
| Clinical characteristics | | | |
| Hypertension n (%) | 220 (45.2) | 577 (39.7) | 499 (40.7) |
| Diabetes (DM) n (%) | 177 (36.3) | 502 (34.5) | 399 (32.5) |
| Hypercholesterolemia n (%) | 324 (66.5) | 967 (66.5) | 841 (68.6) |
| Current Smoking n (%) | 66 (13.6) | 194 (13.3) | 175 (14.3) |
| BMI (SD) (kg/m2) | 28.0 (4.4) | 27.9 (4.3) | 27.6 (4.2) |
| Drugs n (%) | | | |
| Beta-blockers | 216 (44.4) | 636 (43.7) | 527 (43.0) |
| Aspirin/antiplatelet | 384 (78.9) | 1197 (82.3) | 992 (80.9) |
| Lipid-lowering agent | 147 (30.2) | 442 (30.4) | 418 (34.1) |
| Ramipril | 256 (52.6) | 808 (55.6) | 641 (52.3) |
| Vitamin E | 228 (46.8) | 717 (49.3) | 645 (52.6) |

The baseline characteristics of this subset of the HOPE cohort was not significantly different from the whole cohort. Baseline characteristics of the sample segregated by haptoglobin phenotype revealed no significant differences in baseline demographic, clinical or treatment characteristics (Table 4).

The effects of Hp phenotype on CV outcomes: In subjects who did not receive antioxidant therapy there was no significant difference in the incidence of the primary composite endpoint (non-fatal MI, stroke or cardiovascular death) according to haptoglobin phenotype in the entire study sample (Hp 1-1 45/259 17.4%, Hp 2-1 113/737 15.3%, Hp 2-2 95/581 16.4%, $\chi^2$ for trend 0.08, P=0.87). However, consistent with the results reported for the Strong Heart Study hereinabove, (see Example I, and Levy A P, et al. Haptoglobin phenotype is an independent risk factor for cardiovascular disease in individuals with diabetes: the strong heart study. J Am Coll Card 2002; 40: 1984-1990) we found that in DM patients of the HOPE study who did not receive antioxidant therapy, there was an increased risk of the primary composite endpoint (non-fatal MI, stroke or cardiovascular death) associated with the Hp 2 allele (Hp 1-1 13/79 16.5%, Hp 2-1 44/225 19.6%, Hp 2-2 48/187 25.7%, $\chi^2$ for trend 5.67, P=0.02).

The effects of vitamin E on CV outcomes: Table 5 below presents the results of analysis of primary CV outcomes (non-fatal MI, stroke or cardiovascular death) with and without Vitamin E supplementation, in correlation with haptoglobin phenotypes, for all patients and for diabetic (DM) patients.

TABLE 5

Relative Risk Ratio for CV outcomes and Vitamin E supplementation

|  | Hp 1-1 | Hp 2-1 | Hp 2-2 |
|---|---|---|---|
| All patients | | | |
| N | 487 | 1454 | 1226 |
| Primary (95% CI) | 0.97 (0.63-1.50) | 0.96 (0.74-1.25) | 0.92 (0.69-1.22) |
| p-value | NS | NS | NS |

TABLE 5-continued

Relative Risk Ratio for CV outcomes and Vitamin E supplementation

|  | Hp 1-1 | Hp 2-1 | Hp 2-2 |
|---|---|---|---|
| CV death (95% CI) | 1.10 (0.56-2.12) | 1.07 (0.69-1.64) | 0.75 (0.48-1.16) |
| p-value | NS | NS | NS |
| MI (95% CI) | 0.79 (0.47-1.33) | 1.02 (0.75-1.38) | 0.94 (0.68-1.30) |
| p-value | NS | NS | NS |
| Stroke (95% CI) | 1.50 (0.56-4.04) | 0.92 (0.53-1.60) | 0.85 (0.46-1.57) |
| p-value | NS | NS | NS |
| DM Patients only | | | |
| N | 177 | 502 | 399 |
| Primary (95% CI) | 0.84 (0.40-1.79) | 1.08 (0.72-1.61) | 0.70 (0.45-1.10) |
| p-value | NS | NS | NS |
| CV death (95% CI) | 0.64 (0.21-1.92) | 1.0 (0.53-1.93) | 0.45 (0.23-0.90) |
| p-value | NS | NS | * |
| MI (95% CI) | 0.83 (0.33-2.06) | 0.99 (0.45-2.18) | 0.57 (0.33-0.97) |
| p-value | NS | NS | * |
| Stroke (95% CI) | 2.24 (0.41-12.4) | 0.99 (0.45-2.18) | 1.15 (0.47-2.82) |
| p-value | NS | NS | NS |

RRR are given as mean (95% CI) for the risk of a CV event with vitamin E as compared to without vitamin E.
*, statistically significant with p < 0.05.
NS, not statistically significant.

In the entire sample studied there was no significant benefit associated with vitamin E supplementation for any of the primary CV outcomes regardless of haptoglobin type (Table 5, all patients). Furthermore, as previously reported (The Heart Outcomes Prevention Evaluation Study Investigators. Vitamin E supplementation and cardiovascular events in high-risk patients. N Eng J Med 2000; 342: 154-160) (Table 5, DM patients), there was no significant benefit of vitamin E supplementation in the unselected DM group. Surprisingly, it was found that in DM patients with the haptoglobin 2-2 phenotype, vitamin E therapy significantly lowered the risk of CV death (RR 0.45, 95% CI 0.23-0.90; P=0.003) and significantly lowered the risk of non-fatal myocardial infarction (MI) (RR 0.57, 95% CI 0.33-0.97; P=0.02), while no significant benefit of vitamin E therapy was evident in DM patients any of the other haptoglobin phenotypes (Hp 1-1 and Hp 2-1) for any of the primary CV outcomes.

The effects of ramipril on CV outcomes: Table 6 below presents the results of analysis of primary CV outcomes (non-fatal MI, stroke or cardiovascular death) with and without Ramipril supplementation, in correlation with haptoglobin phenotypes, for all patients and for diabetic (DM) patients.

TABLE 6

Relative Risk Ratio for CV outcomes and Ramipril supplementation

|  | Hp 1-1 | Hp 2-1 | Hp 2-2 |
|---|---|---|---|
| All patients | | | |
| N | 453 | 1349 | 1129 |
| Primary (95% CI) | 0.74 (0.47-1.17) | 0.81 (0.62-1.07) | 0.76 (0.57-1.02) |
| p-value | NS | NS | NS |
| CV death (95% CI) | 0.58 (0.29-1.18) | 1.02 (0.66-1.58) | 0.87 (0.55-1.37) |
| p-value | NS | NS | NS |

TABLE 6-continued

Relative Risk Ratio for CV outcomes and Ramipril supplementation

|  | Hp 1-1 | Hp 2-1 | Hp 2-2 |
| --- | --- | --- | --- |
| MI (95% CI) | 0.61 (0.35-1.06) | 0.88 (0.64-1.20) | 0.83 (0.59-1.17) |
| p-value | NS | NS | NS |
| Stroke (95% CI) | 0.91 (0.33-2.51) | 0.68 (0.38-1.21) | 0.53 (0.27-1.04) |
| p-value | NS | NS | NS |
| DM Patients only | | | |
| N | 177 | 502 | 399 |
| Primary (95% CI) | 0.78 (0.35-1.75) | 0.97 (0.72-1.61) | 0.57 (0.36-0.90) |
| p-value | NS | NS | * |
| CV death (95% CI) | 0.42 (0.13-1.36) | 0.97 (0.50-1.88) | 0.56 (0.28-1.12) |
| p-value | NS | NS | NS |
| MI (95% CI) | 0.53 (0.19-1.46) | 0.99 (0.81-2.13) | 0.57 (0.38-1.12) |
| p-value | NS | NS | NS |
| Stroke (95% CI) | 1.29 (0.21-7.82) | 0.58 (0.25-1.34) | 0.42 (0.16-1.09) |
| p-value | NS | NS | NS |

* statistically significant p < 0.05.
NS, not statistically significant. RRR are given as mean (95% CI) for the risk of a CV event with ramipril as compared to without ramipril.

As is evident from the analysis of the entire sample, no significant benefit was associated with ramipril supplementation for any of the primary CV outcomes regardless of haptoglobin type (Table 6, all patients). And, similar to the effects of Vitamin E, (Table 5, DM patients), there was no significant benefit of ramipril supplementation in the unselected DM group. Surprisingly, a significant benefit from ramipril for the composite primary endpoint of stroke, CV death and myocardial infarction was observed only in those diabetic (DM) patients with the haptoglobin 2-2 phenotype (RR 0.57, 95% CI 0.36-0.90; P<0.05). There was no benefit to ramipril in any of the other haptoglobin phenotypes (Hp 1-1, Hp 1-2) for any of the primary CV outcomes (Table 6).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

LIST OF REFERENCES

1. Howard B V, Magee M F. Diabetes and Cardiovascular Disease. Curr Atheroscler Rep 2000; 2; 476-481.
2. Aronson D, Rayfield E J. Diabetes in Textbook of Cardiovascular Medicine. Topol E J ed. Philadelphia, Lippincott-Raven Publishers, 1998: 171-194.
3. Stamler J, Vaccaro O, Neaton J D, Wentworth D. Diabetes, other risk factors and 12-year cardiovascular mortality for men screened in the multiple risk factor intervention trial. Diab Care 1993; 16: 434-444.
4. Kannel W, McGee D. Diabetes and glucose tolerance as risk factors for cardiovascular disease. The Framingham Study. Diab Care 1979; 2: 120-126.
5. Jarrett R J, Shipley M J. Type 2 (non-insulin dependent) diabetes mellitus and cardiovascular disease-putative association via common antecedents: Further evidence from the Whitehall Study. Diabetologia 1988; 31: 737-740.
6. Fontbonne A, Eschwege E, Cambien F, et al. Hypertryglyceridemia as a risk factor for coronary artery disease mortality in subjects with impaired glucose tolerance or diabetes: Results from the 11-year follow up of the Paris Prospective Study. Diabetologia 1989; 32: 300-304.
7. Donahue R P, Orchard T G. Diabetes mellitus and macrovascular complications. An epidemiological perspective. Diab Care 1992; 15: 1141-1155.
8. Barret-Connor E, Cohn B, Wingard D, Edelstein S L. Why is diabetes mellitus a stronger risk factor for fatal ischemic heart disease in women then in men? The Rancho Bernardo Study. JAMA 1991; 265: 627-631.
9. Hammoud T, Tanguay J F, Bourassa M G. Management of coronary artery disease: therapeutic options in patients with diabetes. J Am Coll Card 2000; 36: 355-365.
10. Head J, Fuller J H. International variations in mortality among diabetic patients. The WHO Multinational Study of Vascular Disease in Diabetics. Diabetologia 1990; 33: 447-481.
11. Grimaldi A, Heurtier A. Epidemiology of cardiovascular complications of diabetes. Diab Metab 1999; 3: 12-20.
12. Woods K L, Samanta A, Burden A C. Diabetes mellitus as a risk factor for acute myocardial infarction in Asians and Europeans. Br Ht J 1989; 62: 118-122.
13. Cruickshank J K, Alleyne S A. Black West Indian and matched white diabetics in Britain compared with diabetics in Jamaica: body mass, blood pressure and vascular disease. Diab Care 1987; 10: 170-179.
14. UK Prospective Diabetes Study Group. Ethnicity and cardiovascular disease. The incidence of myocardial infarction in white, south Asian and afro-Caribbean patients with type 2 diabetes. Diab Care 1998; 21: 1271-1277.
15. Mather H M, Chaturvedi N, Fuller J H. Mortality and morbidity from diabetes in south Asians and Europeans: 11-year follow up of the southall diabetes survey, London, UK. Diab Med 1998; 15: 53-59.
16. Chaturvedi N, Jarrett J, Morrish N, Keen H, Fuller J H. Differences in mortality and morbidity in African-Caribbean and European people with non-insulin dependent diabetes mellitus: results of 20 year follow up of a London cohort of a multinational study. Brit Med J 1996; 313: 848-852.
17. Chaturverdi N, Fuller J H. Ethnic differences in mortality from cardiovascular disease in the UK: do they persist in people with diabetes? J Epid Comm Health 1996; 50: 137-139.
18. Samanta A, Burden A C, Jagger C. A comparison of the clinical features and vascular complications of diabetes between migrant Asians and Caucasians in Leicester, UK. Diab Res Clin Pract 1991; 14: 205-213.
19. Hoy W, Kelly A, Jacups S, et al. Stemming the tide: reducing cardiovascular disease and renal failure in Australian Aborigines. Aust N Z J Med 1999; 29: 480-483.
20. Howard B V, Lee E T, Cowan L D, et al. Rising tide of cardiovascular disease in American Indians. The Strong Heart Study. Circ 1999; 99: 2389-2395.
21. Dobryszycka W. Biological functions of haptoglobin-new pieces to an old puzzle. Eur J Clin Chem 1997; 35: 647-654.
22. Bowman B H, Kurosky A. Haptoglobin: the evolutionary product of duplication, unequal crossing over, and point mutation. Adv Hum Gen 1982; 12: 189-261.
23. Langlois M R, Delanghe J R. Biological and clinical significance of haptoglobin polymorphism in humans. Clin Chem 1996; 42: 1589-1600.
24. Delanghe J, Langlois M, Ouyang J, Claeys G, De Buyzere M, Wuyts B. Effect of haptoglobin phenotypes on growth of *Streptococcus* pyogenes. Clin Chem Lab Med 1998; 36: 691-696.
25. Quaye I K, Ekuban F A, Goka B Q, et al. Haptoglobin 1-1 is associated with susceptibility to severe *Plasmodium falciparum* malaria. Trans R Soc Trop Med Hyg 2000; 94: 216-219.
26. Giblett E R. Genetic Markers in Human Blood. Oxford, Blackwell Scientific, 1969: 63-125.
27. Levy A P, Roguin A, Marsh S, et al. Haptoglobin phenotype and vascular complications in diabetes. N Eng J Med 2000; 343: 369-370.
28. Nakhoul F, Marsh S, Hochberg I, Leibu R, Miller B, Levy A P. Haptoglobin phenotype and diabetic retinopathy. JAMA 2000; 284: 1244-1245.
29. Nakhoul F, Zoabi R, Kantor Y, et al. Haptoglobin phentotype and diabetic nephropathy. Diabetologia 2001; in press.
30. Roguin A, Hochberg I, Nikolsky E, et al. Haptoglobin phenotype as a predictor of restenosis after percutaneous transluminal coronary angioplasty. Am J Card 2001; 87: 330-332.
31. Delanghe J, Cambier B, Langlois M, et al. Haptoglobin polymorphism, a genetic risk factor in coronary artery bypass surgery. Atheroscler 1997; 132: 215-219.
32. Chapelle J P, Albert A, Smeets J P, Heusghem C, Kulbertus H E. Effect of the haptoglobin phenotype on the size of a myocardial infarct. N Eng J Med 1982; 307: 457-463.
33. Delanghe J R, Duprez D A, De Buyzere M L, et al. Haptoglobin polymorphism and complications in established essential arterial hypertension. J Hyper 1993; 11: 861-867.
34. Surya Prabha P, Padma T, Ramaswamy M. Haptoglobin patterns in essential hypertension and associated conditions-increased risk for Hp 2-2. Hum Herid 1987; 37: 345-348.
35. Golabi P, Kshatriya G K, Kapoor A K. Association of genetic markers with coronary heart disease (myocardial infarction)-a case-control study. J Ind Med Assoc 1999; 97: 6-7.
36. Hong S H, Kang B Y, Lim J H, et al. Haptoglobin polymorphism in Korean patients with cardiovascular disease. Hum Herid 1997; 47: 283-287.
37. Bilgrami G, Tyagi S P, Qasim A. Serum haptoglobin in cases of ischemic heart disease. Jpn Heart J 1980; 21: 505-510.
38. Frohlander N, Johnson O. Haptoglobin groups in acute myocardial infarction. Hum Herid 1989; 39: 345-350.
39. Lee E T, Welty T K, Fabsitz R, et al. The Strong Heart Study: a study of cardiovascular disease in American Indians: design and methods. Am J Epid 1990; 132: 1141-1155.
40. Howard B V, Welty T K, Fabsitz R, et al. Risk factors for coronary heart disease in diabetic and nondiabetic North Americans: the Strong Heart Study. Diabetes 1992: 41: 4-11.
41. WHO Expert Committee on Diabetes Mellitus. Second Report. Geneva, World Health Organization. 1980 (technical report series 646).
42. Lee E T, Cowan L D, Howard W J, et al. All cause mortality and cardiovascular disease mortality I3 American Indian populations aged 45 to 74 years, 1984 to 88: the Strong Heart Study. Am J Epidem 1998; 147: 995-1008.
43. Howard B V, Lee E T, Cowan L D, et al. Coronary heart disease prevalence and its relation to risk factors in American Indians: the Strong Heart Study. Am J Epidem 1995; 142: 254-268.
44. Linke R P. Typing and subtyping of haptoglobin from native serum using disc gel electrophoresis in alkaline buffer: application to routine screening. Anal Biochem 1984; 141: 55-61.
45. Wassell J, Keevil B. A new method for haptoglobin phenotyping. Ann Clin Biochem 1999; 36: 609-612.
46. Smithies O. Zone electrophoresis in starch gels: group variations in the serum proteins of normal human adults. Biochem 1955; 61: 629-641.
47. McGill M J, Donnelly R, Molyneaux L, Yue D K. Ethnic differences in the prevalence of hypertension and proteinuria in NIDDM. Diab Res Clin Pract 1996; 33: 173-179.
48. Habib G, Heibig J, Forman S, et al. Influence of coronary artery collateral vessels on myocardial infarct size in humans. Results of phase 1 thrombolysis in myocardial infarction (TIMI) trial. Circulation 1991; 83: 739-746.
49. Guigliano D, Ceriello A, Paolisso G. Oxidative stress and diabetic vascular complications. Diab Care 1996; 19: 257-267.
50. Nishikawa T, Edelstein D, Brownlee M. The missing link: a single unifying mechanism for diabetic complications. Kid Int 2000; 58 (S77): S26-S30.
51. Kristiansen M, Graversen J H, Jacobsen C, et al. Identification of the hemoglobin scavenger receptor. Nature 2001; 409: 198-201.
52. Resnick D, Pearson A, Krieger M. The SRCR superfamily: a family reminiscent of the Ig superfamily. Trends Biochem Sci 1994; 19: 5-8.
53. Nathan C F, Murray H W, Cohn Z A. Current concepts: the macrophage as an effector cell. N Eng J Med 1980; 303: 622-626.
54. Goldstein J L, Ho Y K, Basu S K, Brown M S. Binding site of macrophages that mediates uptake and degradation of acetylated low-density lipoprotein, producing massive cholesterol deposition. Proc Natl Acad Sci USA 1979; 76: 333-337.
55. Rosenfeld M E, Khoo J C, Miller E, Parthasarthy S, Palinski W, Witzum J L. Macrophage-derived foam cells freshly isolated from rabbit atherosclerotic lesions degrade modified lipoproteins, promote oxidation of low-density lipoproteins, and contain oxidation specific lipid protein adducts. J Clin Invest 1990; 87: 90-99.
56. Van den Heuvel M M, Tensen C P, van As J H, et al. Regulation of CD163 on human macrophages: cross-linking of CD163 induces signaling and activation. J Leuk Biol 1999; 66: 858-866.

57. Wagner L, Gessl A, Baumgartner Parzer S, Base W, Waldhausl W, Pastemack M S. Haptoglobin phenotyping by newly developed monoclonal antibodies. Demonstration of haptoglobin uptake into peripheral blood neutrophils and monocytes. J 1 mm 1996; 156: 1989-1996.
58. El Ghmati S M, Van Hoeyveld E M, Van Strijp J A G, Ceuppens J L, Stevens E A M. Identification of haptoglobin as an alternative ligand for CD11b/CD18. J Imm 1996; 156: 2542-2552.
59. Chia M C. The role of adhesion molecules in atherosclerosis. Crit Rev Clin Lab Sci 1998; 35: 573-602.
60. Epstein S E, Zhu J, Burnett M S, Zhou Y F, Vercellotti G, Hajjar D. Infection and atherosclerosis: potential roles of pathogen burden and molecular mimicry. Art Thromb Vasc Biol 2000; 20: 1417-1420.

(LAR), Self-Sustained Synthetic Reaction (3R/NASBA) and Q-Beta (Qβ) Replicase reaction.

8. The method of claim 6, wherein said direct detection method is selected from the group consisting of a cycling probe reaction (CPR) and a branched DNA analysis.

9. The method of claim 6, wherein said detection of at least one sequence change employs a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis and Dideoxy fingerprinting (ddF).

---

---

What is claimed is:

1. A method of determining a potential of a diabetic patient over 55 years of age to benefit from vitamin E therapy for prevention of myocardial infarction, the method comprising determining a haptoglobin phenotype of the diabetic patient and thereby determining the potential of the diabetic patient to benefit from said vitamin E therapy, wherein said benefit from said vitamin E therapy to a patient having a haptoglobin 2-2 phenotype is greater compared to patients having haptoglobin 1-2 phenotype or haptoglobin 1-1 phenotypes.

2. The method of claim 1, wherein said determining said haptoglobin phenotype is effected by directly determining the haptoglobin phenotype of the diabetic patient.

3. The method of claim 2, wherein step of determining said haptoglobin phenotype is effected by an immunological detection method.

4. The method of claim 3, wherein said immunological detection method is selected from the group consisting of a radio-immunoassay (RIA), an enzyme linked immunosorbent assay (ELISA), a western blot, an immunohistochemical analysis, and fluorescence activated cell sorting (FACS).

5. The method of claim 1, wherein said determining said haptoglobin phenotype is effected by determining a haptoglobin genotype of the diabetic patient.

6. The method of claim 5, wherein said step of determining said haptoglobin genotype of the diabetic patient is effected by a method selected from the group consisting of a signal amplification method, a direct detection method and detection of at least one sequence change.

7. The method of claim 6, wherein said signal amplification method is selected from the group consisting of PCR, LCR 10. The method of claim 6, wherein said signal amplification method amplifies a molecule selected from the group consisting of a DNA molecule and an RNA molecule.

11. A method of determining the importance of reducing oxidative stress by administering vitamin E in a diabetic patient over 55 years of age so as to prevent myocardial infarction, the method comprising the step of determining a haptoglobin phenotype of the diabetic patient thereby determining the importance of reducing the oxidative stress by administering vitamin E in the specific diabetic patient, wherein said importance of reducing oxidative stress by administering vitamin E is greater in a patient having a haptoglobin 2-2 phenotype compared to patients having haptoglobin 1-2 phenotype or haptoglobin 1-1 phenotypes.

12. The method of claim 11, wherein said step of determining said haptoglobin phenotype is effected by directly determining the haptoglobin phenotype of the diabetic patient.

13. The method of claim 12, wherein said step of determining said haptoglobin phenotype is effected by an immunological detection method.

14. The method of claim 13, wherein said an immunological detection method is selected from the group consisting of a radio-immunoassay (RIA), an enzyme linked immunosorbent assay (ELISA), a western blot, an immunohistochemical analysis, and fluorescence activated cell sorting (FACS).

15. The method of claim 11, wherein said determining said haptoglobin phenotype is effected by determining a haptoglobin genotype of the diabetic patient.

16. The method of claim 15, wherein said step of determining said haptoglobin genotype of the diabetic patient is effected by a method selected from the group consisting of a signal amplification method, a direct detection method and detection of at least one sequence change.

17. The method of claim 16, wherein said signal amplification method is selected from the group consisting of PCR, LCR (LAR), Self-Sustained Synthetic Reaction (3R/NASBA) and Q-Beta (Qβ) Replicase reaction.

18. The method of claim 16, wherein said direct detection method is selected from the group consisting of a cycling probe reaction (CPR) and a branched DNA analysis.

19. The method of claim 16, wherein said detection of at least one sequence change employs a method selected from the group consisting of restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis and Dideoxy fingerprinting (ddF).

20. The method of claim 16, wherein said signal amplification method amplifies a molecule selected from the group consisting of a DNA molecule and an RNA molecule.

* * * * *